(12) United States Patent
Suranyi et al.

(10) Patent No.: US 10,321,680 B2
(45) Date of Patent: Jun. 18, 2019

(54) MIXTURES OF SABADILLA ALKALOIDS AND DILL SEED OIL AND USES THEREOF

(71) Applicant: McLaughlin Gormley King Company, Golden Valley, MN (US)

(72) Inventors: Robert A. Suranyi, Minneapolis, MN (US); Donald L. Sundquist, Minneapolis, MN (US)

(73) Assignee: MCLAUGHLIN GORMLEY KING COMPANY, Golden Valley, MN (US)

( * ) Notice: Subject to any disclaimer, the term of this patent is extended or adjusted under 35 U.S.C. 154(b) by 0 days.

(21) Appl. No.: 15/637,335

(22) Filed: Jun. 29, 2017

(65) Prior Publication Data

US 2018/0000081 A1    Jan. 4, 2018

Related U.S. Application Data

(60) Provisional application No. 62/357,894, filed on Jul. 1, 2016.

(51) Int. Cl.

| | | |
|---|---|---|
| *A01N 43/42* | (2006.01) | |
| *A01N 45/00* | (2006.01) | |
| *A01N 65/00* | (2009.01) | |
| *A01N 65/10* | (2009.01) | |
| *A01N 65/40* | (2009.01) | |

(52) U.S. Cl.
CPC ............ *A01N 43/42* (2013.01); *A01N 45/00* (2013.01); *A01N 65/00* (2013.01); *A01N 65/10* (2013.01); *A01N 2300/00* (2013.01); *Y02A 50/324* (2018.01); *Y02A 50/326* (2018.01); *Y02A 50/328* (2018.01); *Y02A 50/329* (2018.01); *Y02A 50/33* (2018.01)

(58) Field of Classification Search
None
See application file for complete search history.

(56) References Cited

U.S. PATENT DOCUMENTS

| | | | |
|---|---|---|---|
| 9,034,401 B1 * | 5/2015 | Clarot | A61K 36/515 424/758 |
| 2002/0173436 A1 | 11/2002 | Sonnenberg et al. | |
| 2007/0264297 A1 | 11/2007 | Scialdone et al. | |
| 2012/0148653 A1 | 6/2012 | Jones | |

FOREIGN PATENT DOCUMENTS

WO    2016054318 A1    4/2015

OTHER PUBLICATIONS

International Search Report and Written Opinion for corresponding PCT Application No. PCT/US17/39901 dated Sep. 28, 2017.

\* cited by examiner

*Primary Examiner* — Robert A Wax
*Assistant Examiner* — Quanglong N Truong
(74) *Attorney, Agent, or Firm* — Wood, Phillips, Katz, Clark & Mortimer

(57) ABSTRACT

The present invention is directed to pesticidal mixtures comprising sabadilla alkaloids and dill seed oil and methods of controlling pests including insects and mites by application of pesticidal mixtures comprising sabadilla alkaloids and dill seed oil.

18 Claims, No Drawings

MIXTURES OF SABADILLA ALKALOIDS AND DILL SEED OIL AND USES THEREOF

FIELD OF THE INVENTION

The present invention is directed to pesticidal mixtures comprising sabadilla alkaloids and dill seed oil and methods of controlling pests including insects and mites by application of pesticidal mixtures comprising sabadilla alkaloids and dill seed oil.

BACKGROUND OF THE INVENTION

Arthropod pests are one of the major threats to human welfare and exert continued stress on the food supply and transmit a broad array of medical and veterinary diseases. Synthetic insecticides played a significant role and in many ways ushered in modern agriculture and pest control. However, the widespread use of synthetic insecticides also created numerous environmental challenges. The acute effects of synthetic pesticides on professional applicators and other end users are well-known but the chronic long term human health effects can be equally serious. Further, the use of synthetic insecticides has led to the development of resistant insect populations. Insecticide resistance is a complex phenomenon underlined by a diverse array of physiological mechanisms. Major mechanisms that are responsible for the development of insecticide resistance are metabolic detoxification, target site mutation, reduced cuticular penetration and behavioral avoidance.

Integrated Pest Management ("IPM") is a holistic approach to pest management. A fundamental aspect of insecticide utilization under the broader framework of IPM is the management of insecticide resistance (IRM) by the utilization of insecticide combinations that reduce the rate of resistance development. A combination of insecticides with different modes of action is fundamentally a concept based upon the idea of redundant killing of target insects. Insects adapted to one of the active ingredient in the combination product will still be killed by the other active ingredient. Mixtures can also reduce the amount of pesticides applied in the environment and the environmental impact associated with pesticide applications.

Most botanical insecticides are readily biodegradable and significantly less harmful to the environment and users than synthetic insecticides. The very short environmental persistence, usually less than 24 hours, of plant derived insecticides is favorable to the survival of non-target, beneficial parasites and predators which are important components of IPM. Unlike conventional insecticides which are typically based on a single active ingredient, plant derived insecticides usually comprise an array of chemical compounds that affect both behavioral and physiological functions of the target arthropods. The probability of pest resistance developing to plant derived insecticides is less than that for synthetic pesticides because these mixtures may have a variety of modes of action.

One effective naturally derived pesticide is found in the tissues of many of the plants of the genus *Schoenocaulon*, commonly referred to as sabadilla. The species with the longest history of use, and the most readily available, is *Schoenocaulon officinale*. The plant is indigenous to Central and South America and its seeds have been used for centuries for their insecticidal properties. The seeds contain several alkaloids including veratridine and cevadine, both of which are known to be active against arthropods.

Another effective naturally derived pesticide is dill seed oil, which is extracted from the seeds of *Anethum sowa* or *Anethum graveolens*. The major components of dill seed oil include carvone, dihydrocarvone, dillapiole, limonene. These components have been shown to have insecticidal activity. See Khani A. et al. Chemical composition and insecticide activity of essential oils from dill seeds. 2013. Int'l J Agriculture, 3(3), 489-494. Dill seed oil is safe for use by applicators and other mammals. In fact, dill seed oil has been used for flavoring food consumed by humans for centuries.

Thus, there is a need in the art for pesticide combinations that contain naturally derived pesticides that decrease health concerns to humans and also decrease the risk of the development of pesticide resistance.

SUMMARY OF THE INVENTION

In one aspect, the present invention is directed to pesticidal mixtures of sabadilla alkaloids and dill seed oil ("DSO").

In another aspect, the present invention is directed to methods of controlling pests, including insects and mites, comprising applying an effective amount of a mixture of sabadilla alkaloids and DSO.

In a preferred aspect, the sabadilla alkaloids are derived from *Schoenocaulon officinale*.

DETAILED DESCRIPTION OF THE INVENTION

Applicant unexpectedly discovered that pesticidal mixtures of sabadilla alkaloids and DSO provided enhanced pesticidal activity compared to either pesticide alone. Further, Applicant discovered that pesticidal mixtures of sabadilla alkaloids and DSO were capable of controlling a large variety of arthropods.

The present invention is directed to pesticidal mixtures comprising an effective amount of sabadilla alkaloids and DSO.

Sabadilla alkaloids may be derived from any species of *Schoenocaulon*. The genus *Schoenocaulon* includes the following species: *S. calcicola, S. caricifolium, S. comatum, S. conzattii, S. dubium* (alt. *S. gracile*), *S. framei, S. ghiesbreghtii* (alt. *S. drummondii, S. yucatanense*),*S. ignigenum, S. intermedium, S. jaliscense, S. macrocarpum* (alt. *S. lauricola*),*S. madidorum, S. megarrhizum, S. mortonii, S. oaxacense, S. obtusum, S. officinale, S. pellucidum, S. plumosum, S. pringlei, S. rzedowskii, S. tenorioi, S. tenue, S. tenuifolium, S. texanum*, and *S. tigrense*. In a preferred embodiment the sabadilla alkaloids are derived from *S. officinale*. In another preferred embodiment the saabdilla alkaloids are veratridine and cevadine.

Dill seed oil is extracted from the seeds of *Antheum sowa* or *Anethum graveolens*. The chemical compositions of DSO includes d-carvone, d-limonene, d-phellandrene, α-pinene, diterpene, d-dihydrocarvone, α-phellandrene, β-pinene, 1,8-cineole, β-myrcene, para-cymene, thujone (α-thujone and (β-thujone) and dillapiole. DSO has been shown to have synergistic effects with pyrethrum and pyrethroid insecticides. See U.S. Pat. No. 8,137,715. DSO has also been shown to have insecticidal activity against the American cockroach (*Peripalaneta americana*), the confused flour beetle (*Tribolium castanum*) and the house fly (*Musca domestica*). Babri R A, et al., Chemical composition and insecticidal activity of the essential oil of *Anethum graveolens* L., 2012, Sci Int (Lahore), 24(4), 453-455.

As used herein, all numerical values relating to amounts, weight percentages and the like are defined as "about" or "approximately" each particular value, namely, plus or minus 10%. For example, the phrase "at least 5% by weight" is to be understood as "at least 4.5% to 5.5% by weight." Therefore, amounts within 10% of the claimed values are encompassed by the scope of the claims.

As used herein, w/w denotes weight by weight of the total mixture.

The term "effective amount" means the amount of the formulation that will control the target pest. The "effective amount" will vary depending on the mixture concentration, the type of pest(s) being treated, the severity of the pest infestation, the result desired, and the life stage of the pest during treatment, among other factors. Thus, it is not always possible to specify an exact "effective amount." However, an appropriate "effective amount" in any individual case may be determined by one of ordinary skill in the art.

In a preferred embodiment, the ratio of sabadilla alkaloids to DSO is from about 1:2.5 to about 25:1, preferably from about 1:1 to about 1:10.

In another preferred embodiment, the pesticidal mixtures of the present invention may contain one or more excipients selected from the group consisting of solvents, anti-caking agents, stabilizers, defoamers, slip agents, humectants, dispersants, wetting agents, thickening agents, emulsifiers, penetrants, adjuvants, polymers, propellants and/or preservatives.

The present invention is further directed to methods of controlling a pest comprising applying a pesticidal mixture comprising an effective amount of sabadilla alkaloids and DSO to the pest or the pest's environment.

In a preferred embodiment, the pest is selected from an insect and a mite.

In an embodiment, the pest controlled is selected from the group consisting of aphids (Homoptera), whiteflies (Hemiptera), thrips (Thysanoptera), bed bugs (Hemiptera), fleas (Siphonaptera), caterpillars/worms (Lepidoptera), beetles (Coleoptera), cockroaches (Blattodea), flies (Diptera), ants (Hymenoptera), mosquitoes (Culicidae) and mites (Acari). In a preferred embodiment, the pest controlled are selected from the group consisting of common bed bugs (*Cimex lectularius*), green peach aphids (*Myzus persicae*), house fly (*Musca domestica*), yellow fever mosquito (*Aedes aegypti*), southern house mosquito (*Culex quinquefasciatus*), African malaria mosquito (*Anopheles gambiae*), common malaria mosquito (*Anopheles quadrimaculatus*) and German cockroach (*Blattella germanica*).

The pesticidal mixtures of the present invention can be applied by any convenient means. Those skilled in the art are familiar with the modes of application including spraying, brushing, soaking, in-furrow treatments, pressurized liquids (aerosols), fogging or side-dressing.

In a preferred embodiment, sabadilla alkaloids are applied to the pest or the pest's environment at a rate from about 1 to about 1,000 grams per hectare ("g/HA"), preferably from about 10 to about 700 g/HA and most preferably from about 22 to about 560 g/HA.

In a preferred embodiment, DSO is applied to the pest or the pest's environment at a rate from about 1 to about 10,000 g/HA, more preferably from about 10 to about 7,000 g/HA and most preferably from about 22 to about 5,600 g/HA.

In another preferred embodiment, pesticidal mixtures of the present invention comprise from about 0.05% to about 0.5% w/w sabadilla alkaloids.

In another preferred embodiment, pesticidal mixtures of the present invention comprise from about 0.05% to about 5.0% w/w DSO.

As used herein, "control" a pest or "controlling" pest(s) refers to killing, incapacitating, repelling, or otherwise decreasing the negative impact of the pest on plants or animals to a level that is desirable to the grower or animal.

As used herein, "pest's environment" refers to any area that the pest is present during any life stage. One environment likely to be treated by the methods of the present invention includes the plants that the pest is living on and the surrounding soil. The pest's environment may also include harvested plants, gardens, fields, greenhouses, or other buildings, and various indoor surfaces and structures, such as furniture including beds, and furnishings including books, clothing, etc.

The articles "a," "an" and "the" are intended to include the plural as well as the singular, unless the context clearly indicates otherwise. For example, the methods of the present invention are directed to controlling "pest" but this can include control of a multiple pests (such as a more than one insect or more than one insect species or more than one mite or more than one mite species).

The following examples are intended to illustrate the present invention and to teach one of ordinary skill in the art how to use the extracts of the invention. They are not intended to be limiting in any way.

EXAMPLES

Example 1

German Cockroach

In this study, the response of the German cockroach (*Blattella germanica*) to application of a 1:1 and 1:10 ratio of sabadilla (*S. officinale*) alkaloids to dill seed oil ("DSO") will be observed. Specifically, dabadilla alkaloids and DSO will be applied to the pest at the respective rates of: 1) 0.05% w/w to 0.05% w/w, 2) 0.05% w/w to 0.5% w/w, 3) 0.5% w/w to 0.5% w/w and 0.5% w/w to 5.0% w/w.

The results of the study are predicted to show more than an additive effect. One can determine that the response is synergistic using the following formula: % $C_{exp}$=A+B−(AB/100).

% $C_{exp}$=A+B−(AB/100), where % $C_{exp}$ is the expected efficacy and "in which A and B are the control levels given by the single [insecticides]. If the ratio between the experimentally observed efficacy of the mixture $C_{obs}$ and the expected efficacy of the mixture is greater than 1, synergistic interactions are present in the mixture." (Gisi, *Synergisitic Interaction of Fungicides in Mixtures*, The American Phytopathological Society, 86:11, 1273-1279, 1996). Adopting a conservative approach, Applicant determined synergy to be present at ratios of ≥1.1.

Example 2

House Fly

In this study, the response of the house fly (*Musca domestica*) to application of a 1:1 and 1:10 ratio of sabadilla (*S. officinale*) alkaloids to dill seed oil ("DSO") will be observed. Specifically, sabadilla alkaloids and DSO will be applied to the pest at the respective rates of: 1) 0.05% w/w to 0.05% w/w, 2) 0.05% w/w to 0.5% w/w, 3) 0.5% w/w to 0.5% w/w and 0.5% w/w to 5.0% w/w.

The results of the study are predicted to show more than an additive effect. One can determine that the response is synergistic using the following formula: $\%C_{exp}=A+B-(AB/100)$.

Example 3

Common Bed Bug

In this study, the response of the common bed bug (*Cimex lectularius*) to application of a 1:1 and 1:10 ratio of sabadilla (*S. officinale*) alkaloids to dill seed oil ("DSO") will be observed. Specifically, sabadilla alkaloids and DSO will be applied to the pest at the respective rates of: 1) 0.05% w/w to 0.05% w/w, 2) 0.05% w/w to 0.5% w/w, 3) 0.5% w/w to 0.5% w/w and 0.5% w/w to 5.0% w/w.

The results of the study are predicted to show more than an additive effect. One can determine that the response is synergistic using the following formula: $\%C_{exp}=A+B-(AB/100)$.

Example 4

Green Peach Aphid

In this study, the response of the green peach aphid (*Myzus persicae*) to application of a 1:1 and 1:10 ratio of sabadilla (*S. officinale*) alkaloids to DSO will be observed. Specifically, sabadilla alkaloids and DSO will be applied to the pest at the respective rates of: 1) 22 g/HA and 22 g/HA; 2) 22 g/HA and 224 g/HA; 3) 560 g/HA and 560 g/HA; and 4) 560 g/HA and 5604 g/HA.

The results of the study are predicted to show more than an additive effect. One can determine that the response is synergistic using the following formula: $\%C_{exp}=A+B-(AB/100)$.

What is claimed is:

1. A pesticidal mixture comprising an effective amount of sabadilla alkaloids and dill seed oil.

2. The mixture of claim 1, wherein the sabadilla alkaloids are derived from *Schoenocaulon officinale*.

3. The mixture of claim 1, wherein the sabadilla alkaloids are veratridine and cevadine.

4. The mixture of claim 1, wherein the ratio of sabadilla alkaloids to dill seed oil is from about 1:2.5 to about 25:1.

5. The mixture of claim 1, wherein the ratio of sabadilla alkaloids to dill seed oil is from about 1:1 to about 1:10.

6. The mixture of claim 1, wherein the sabadilla alkaloids are at a concentration from about 0.05% to about 0.5% w/w, wherein w/w denotes weight by total weight of the mixture.

7. The mixture of claim 1, wherein the dill seed oil is at a concentration from about 0.05% to about 5.0% w/w, wherein w/w denotes weight by total weight of the mixture.

8. The mixture of claim 1 further comprising one or more excipients selected from the group consisting of solvents, anti-caking agents, stabilizers, defoamers, slip agents, humectants, dispersants, wetting agents, thickening agents, emulsifiers, penetrants, adjuvants, polymers, propellants and/or preservatives.

9. A method of controlling a pest comprising applying a pesticidal mixture comprising an effective amount of sabadilla alkaloids and dill seed oil to the pest or the pest's environment.

10. The method of claim 9, wherein the pest is at least one of an insect and a mite.

11. The method of claim 9, wherein the pest is selected from the group consisting of aphids (Homoptera), whiteflies (Hemiptera), thrips (Thysanoptera), bed bugs (Hemiptera), fleas (Siphonaptera), caterpillars/worms (Lepidoptera), beetles (Coleoptera), cockroaches (Blattodea), flies (Diptera), ants (Hymenoptera), mosquitoes (Culicidae) and mites (Acari).

12. The method of claim 9, wherein the pest is selected from the group consisting of common bed bugs (*Cimex lectularius*), green peach aphids (*Myzus persicae*), house fly (*Musca domestica*), yellow fever mosquito (*Aedes aegypti*), southern house mosquito (*Culex quinquefasciatus*), African malaria mosquito (*Anopheles gambiae*), common malaria mosquito (*Anopheles quadrimaculatus*) and German cockroach (*Blattella germanica*).

13. The method of claim 9, wherein the sabadilla alkaloids are applied to the pest or the pest's environment at a rate from about 1 to about 1,000 grams per hectare.

14. The method of claim 9, wherein the sabadilla alkaloids are applied to the pest or the pest's environment at a rate from about 10 to about 700 grams per hectare.

15. The method of claim 9, wherein the sabadilla alkaloids are applied to the pest or the pest's environment at a rate from about 22 to about 560 grams per hectare.

16. The method of claim 9, wherein the dill seed oil is applied to the pest or the pest's environment at a rate from about 1 to about 10,00 grams per hectare.

17. The method of claim 9, wherein the dill seed oil is applied to the pest or the pest's environment at a rate from about 10 to about 7,000 grams per hectare.

18. The method of claim 9, wherein the dill seed oil is applied to the pest or the pest's environment at a rate from about 22 to about 5,600 grams per hectare.

* * * * *